United States Patent [19]

Marcker et al.

[11] Patent Number: 4,849,348

[45] Date of Patent: Jul. 18, 1989

[54] POST-TRANSCRIPTIONAL HEME REGULATED HETEROLOGOUS GENE EXPRESSION IN YEAST USING THE LEG HEMOGLOBIN LEADER SEQUENCE

[75] Inventors: Kjeld A. Marcker, Egå ; Erik O. Jensen, Tranbjerg, both of Denmark

[73] Assignee: A/S De Danske Sukkerfabrikker, Copenhagen, Denmark

[21] Appl. No.: 874,069

[22] Filed: Jun. 13, 1986

[30] Foreign Application Priority Data

Oct. 24, 1985 [DK] Denmark .............................. 4889/85

[51] Int. Cl.[4] ...................... C12P 21/00; C12N 15/00; C12N 5/00; C07H 15/12
[52] U.S. Cl. ......................................... 435/68; 435/70; 435/91; 435/172.3; 435/255; 435/256; 435/320; 935/28; 935/37; 935/56; 935/69; 536/27
[58] Field of Search ................... 435/68, 70, 255, 256, 435/320, 193; 536/27; 935/36, 37, 43, 44, 69, 60, 28

[56] References Cited

PUBLICATIONS

Guarente et al, *Cell*, vol. 32, pp. 1279–1286, Apr. 1983, "Heme Regulates Transcription of the CYC1 Gene of *S. cerevisiae* via an Upstream Activation Site".
Hamilton et al, *Proc. Natl. Acad. Sci.*, vol. 79, pp. 7609–7613, Dec. 1982, "Translational Control of Catalase Synthesis by Hemin in the Yeast *Saccharomyces Cerevisiae*".
Cohen et al, *Mol. Gen. Genet.*, 1985, vol. 200, pp. 74–79, "Isolation of the Catalase A Gene of *Saccharomyces cerevisiae*, by Complementation of the cta1 Mutation".
Longridge et al, *EMBO J*, vol. 3(11), pp. 2467–2471, 1927, "Transcription from Maize Storage Protein Gene Promoters in Yeast".
Spevak et al, *Mol. Gen. Genet.*, 1986, vol. 203, pp. 73–78, "Heme Control Region of the Catalase T Gene of the Yeast *Saccharomyces cerevisiae*".
Obstergaard Jensen et al, *EMBO J*, vol. 5 (No. 5), pp. 843–847, 1986, "Heme Regulates the Expression in *Saccharomyces cerevisiae*, of . . . ".
Hyldig–Nielsen et al, *Nucl. Acids Res.*, vol. 10 (2) 1982, pp. 689–700, "The Primary Structures of Two Leghemoglobin Genes from Soybean".

*Primary Examiner*—Robin Lyn Teskin
*Attorney, Agent, or Firm*—Oblon, Fisher, Spivak, McClelland & Maier

[57] ABSTRACT

A method for controlling the level of heterologous gene expression in yeast using a soybean leghemoglobin leader sequence and a suitable promotor. Levels of expression are controlled at the post-transcriptional level by adjusting the amount of heme in the yeast culture medium.

13 Claims, 8 Drawing Sheets

```
----------  ----------  ----------  --GAGATACA  T-TATAATAA  TCTCTCTAGT  GTCATTTAT   TATTTTATCT  GGTGATATAT  605  A
TTCTCTTAAT  ACAATGGAGT  TTTTGTTGAA  CATACATACA  TTTAAAAAAA  AATCTCTAGT  GTCTATTTAC  CC--------  GGTGAG--AA  664  C1
----------  ----TCGAGT  TTTTACTGAA  CATACATTTA  T-TAAAAAAA  ACTCTCTAGT  GTCCATTTAT  TC--------  GGCGAG--AA  639  C2
----------  ----------  ----------  --TATGAAGA  T-TAAAAAAT  ACACTC----  ----------  ----------  ----------  751  C3

ACCTTCTCGT  ----------  ----------  ----------  ----------  ----------  ATACTGTTAT  TT-TTT-CA   ATCTTGTAGA  568  A
GCCTTCTCGT  GTTTTACACA  CTTTAATATT  ATTATATCCT  CAACCCCAC-  --AAAAAAGA  ATACTGTTAT  ATC-TTTCCA  AACCTGTAGA  578  C1
GCCTTCTCGT  GCTTTACACA  CTTTAATATT  ATTATATCCC  CACCCCCACC  AAAAAAAAAA  AAACTGTTAT  ATC-TTTCCA  -----GTACA  546  C2
--------AT  ATATATGCCA  TAAGAACCAA  CAAAAGTACT  ATTTAAGAAA  AGAAAAAAAA  AACCTGCTAC  ATAATTTCCA  ATCTTGTAGA  669  C3

TTTACTTCTT  TT--------A TTTTTATAAA  AAAGACTTTA  ---TTTTTT   TAAAAAA--A  ATAAAGTGAA  ----------  ----TTATTTA 511  A
TTTATTTATT  TATTTATTTA  TTTTTACAAA  GGAGACTTCA  GAAAGTAAT   TACATAA---  AGATAGTGAA  CATCATT---  ---TTATTTA  497  C1
TTTATTTCTT  ----------  TTTTTACAAA  GGAAACTTCA  CGAAAGTAAT  TACAAAA--A  AGATAGTGAA  CATCATT---  ---TTTTTAG  473  C2
TTTATTTCTT  TT--------  TTTTTATAAA  GGAGAGTTAA  --AAA--AAT  TACAAAATAA  AAATAGTGAA  CATCGTCTAA  GCATTTTTAT  590  C3

----------  TTTTGAAAAC  ATGCTCTTTG  ACAATTTTC-  ----------  ----------  ----------  ----------  ----------  482  A
TTATAATAAA  CTTTAAAATC  AAACTTTTT   ATATTTT---  ----------  ----------  ----------  ----------  ----------  459  C1
TTAAGATGAA  TTTTAAAATC  ACACTTTTTT  ATATTTTT-   ----------  ----------  ----------  ----------  ----------  434  C2
ATAAGATGAA  TTTTAAAAA-  ---------T  ATAATTTTTT  TGTCTAAATC  GTCTGTATCT  TGTCTTAGAG  CCATTTTTGT  TTAAATTGGA  510  C3

----------  ----------  ----------  ----------  -----TG     TTTTCCTTTT  CATCATTGGG  TTAAATCTCA  TAGTGCCTCT  440  A
----------  ----------  ----------  ----------  -----TG     TTACCCTTTT  CATTATTGGG  TGAAATCTCA  TAGTGAAGCC  417  C1
----------  ----------  ----------  ----------  -----TG     TTACCCTTTT  CATTATTGGG  TGAAATCTCA  TAGTGAAACT  392  C2
TAAGATCACA  CTATAAAGTT  CTTCCTCCGA  GTTTGATATA  AAAAAAATTG  TTTCCCTTTT  GATTATTGGA  TAAAATCTCG  TAGTGACATT  420  C3
```

POST-TRANSCRIPTIONAL HEME REGULATED HETEROLOGOUS GENE EXPRESSION IN YEAST USING THE LEGHEMOGLOBIN LEADER SEQUENCE

The invention relates to a novel method for the expression of genes in yeast, and DNA fragments as well as plasmids comprising said DNA fragments to be used when carrying out the method.

In the description i.a. the following terms are used:

Promoter region: A DNA fragment containing a promoter and target sequences for RNA polymerase as well as possible activation regions comprising target sequences for transcriptional effector substances.

Effector substance: Substances exerting or mediating a regulator function. Thus the effector substances also include substances influencing the concentration of substances exerting or mediating a regulatory function.

Leader sequence: Generally is meant a DNA sequence being transcribed into a mRNA, but not further translated into protein. The leader sequence comprises thus the DNA fragment from the transcription start to the ATG translation start condon.

Leader sequence: In relation to the present invention is meant a short DNA fragment typically having 40–70 bp and comprising target sequences for a post transcriptional regulation exerted or mediated by intracellular heme.

Furthermore the following terms generally known to persons skilled in the art of molecular biology are used.

CAP addition site: The site where 7-methyl-GTP is added.

DNA sequence or DNA segment: A linear array of nucleotides interconnected through phosphodiester bonds between the 3' and 5' carbon atoms of adjacent pentoses.

Expression: The process undergone by a structural gene to produce a polypeptide. It is a combination of transcription and translation as well as possible post-translational modifications.

Flanking regions: DNA sequences surrounding coding regions. 5' flanking regions contain a promoter. 3' flanking regions may contain transcriptional terminator signals etc.

Gene: A DNA sequence composed of three of four parts (1) the coding sequence for the gene product, (2) the sequences in the promoter region which control whether or not the gene will be expressed, (3) those sequences in the 3' end conditioning the transcriptional termination and optional polyadenylation, as well as (4) intervening sequences, if any.

Intervening sequences: DNA sequences within a gene which are not coding for any peptide fragment. The intervening sequences are transcribed into pre-mRNA and are eliminated by modification of precursorRNA into mRNA.

Cloning: The process of obtaining a population of organisms or DNA sequences deriving from one such organism or sequence by asexual reproduction, or more particular:

the process of isolating a particular organism or part thereof, and the propagation of this subfraction as a homogeneous population.

Coding sequence: DNA sequence determining the amino acid sequence of a polypeptide.

Messenger-RNA (mRNA): RNA molecule produced by transcription of a gene and possible modification of precursorRNA. The mRNA molecule mediates the genetic message determining the amino acid sequence of a polypeptide by part of the mRNA molecule being translated into said peptide. Nucleotide: A monomeric unit of DNA or RNA consisting of a sugar moiety (pentose), a phosphate, and a nitrogenous heterocyclic base. The base is linked to the sugar moiety via a glucosidic bond (1' carbon of the pentose), and this combination of base and sugar is a nucleoside. The base characterizes the nucleotide. The four DNA bases are adenine (A), guanine (G), cytosine (C), and thymine (T). The four RNA bases are A, G, C, and uracil (U).

Plasmid: A nonchromosomal double-stranded DNA sequence comprising an intact replicon such that the plasmid is replicated in a host cell. When the plasmid is placed within a unicellular organism, the characteristics of that organism are changed or transformed as a result of the DNA of the plasmid. For instance a plasmid carrying the gene for tetracycline resistance ($Tc^R$) transforms a cell previously sensitive to tetracycline into one which is resistant to it. A cell transformed by a plasmid is called a transformant.

Polypeptide: A linear array of amino acids interconnected by means of peptide bonds between the α-amino and carboxy groups of adjacent amino acids.

Recombination: The creation of a new DNA molecule by combining DNA fragments of different origin.

Replication: A process reproducing DNA molecules.

Repilcon: A self-replicating genetic element possessing an origin for the initiation of DNA replication and genes specifying the functions necessary for controlling the replication.

Restriction fragment: A DNA fragment resulting from double-stranded cleavage by an enzyme recognizing a specific target DNA sequence.

RNA polymerase: Enzyme exerting the transcription of DNA into RNA.

Transformation: The process whereby a cell is incorporating a plasmid.

Translation: The process of producing a polypeptide from mRNA or:

the process whereby the genetic information present in an mRNA molecule directs the order of specific amino acids during the synthesis of a polypeptide.

Transcription: The method of synthesizing a complementary RNA sequence from a DNA sequence.

Vector: A plasmid, phage DNA or other DNA sequences capable of replication in a host cell and having one or a small number of endonuclease recognition sites at which DNA sequences may be cleaved in a determinable manner without attendant loss of an essential biological function of the DNA, e.g. replication, production of coat proteins or loss of promoter or binding sites, and which contain a marker suitable for use in the identification of transformed cells in the form of for instance tetracycline resistance or ampicillin resistance. A vector is often called a cloning vehicle.

The production of a biologically active product by means of recombinant DNA technology is a complex matter which involves many process steps from the initiation of the transcription to the final achievement of the biologically active molecule.

Many of these process steps do not appear in procaryotic organisms the reason why eucaryotic production organisms must be used in many cases.

Yeast is an eukaryotic organism, the synthesis apparatus of which comprises many of the processes and regulating mechanisms characteristic of higher organisms.

In addition yeast cells have a short generation time and a thousand-year old experience basis exists for the use of yeast as a culture organism.

Completely decisive factors for a biological synthesis of a desired gene product are a possibility and improvement of transcriptional initiation as well as transcriptional and posttranscriptional regulation of the gene expression.

These functions are mainly carried out by 5' flanking regions. A wide range of 5' flanking regions of prokaryotic and eukaryotic genes has been sequenced, and inter alia based thereon a comprehensive knowledge has been provided of the regulation of gene expression and of the subregions and sequences being of importance for the regulation of expression of the gene. Great differences exist in the regulatory mechanism in procaryotic and eucaryotic organisms, but within these two groups there are many common features.

The regulation so the gene expression may take place on the transcriptional level and then it is preferably exerted by regulation of the initiation frequency of transcription. The latter is well known and described inter alia by Benjamin Lewin, Gene Expression, John Weily & Sons, vol. I. 1974, vol. II, Second Edition 1980, vol. III, 1977. Alternatively the regulation may be exerted at the posttranscriptional level e.g. the regulation of the frequency of the translation initiation at the rate of translation and of the termination of translation.

Leghemoglobins are monomeric hemoproteins exclusively synthesized in the root nodules which develop through the symbiotic association of Rhizobia with leguminous plants. A logical candidate for an effector substance activating the leghemoglobin genes is heme produced in Rhizobia and constituting the prostetic group of the leghemoglobins. The synthesis of several hemoproteins in the yeast *Saccharomyces cerevisiae* is also regulated by the level of intracellular heme which also forms the prostetic group of these proteins. Thus the transcription of the isocytochrome c gene is heme dependant while in the case of catalase $T_1$ the heme control is exerted both at the transcriptional and the posttranscriptional level.

BRIEF DESCRIPTION OF THE FIGURES

FIGS. 1A–1B depicts the nucleotide sequence of the 5' regions of the soybean Lba, Lbc1, Lbc2 and Lbc3 leghemoglobin genes.

Figure 1B:
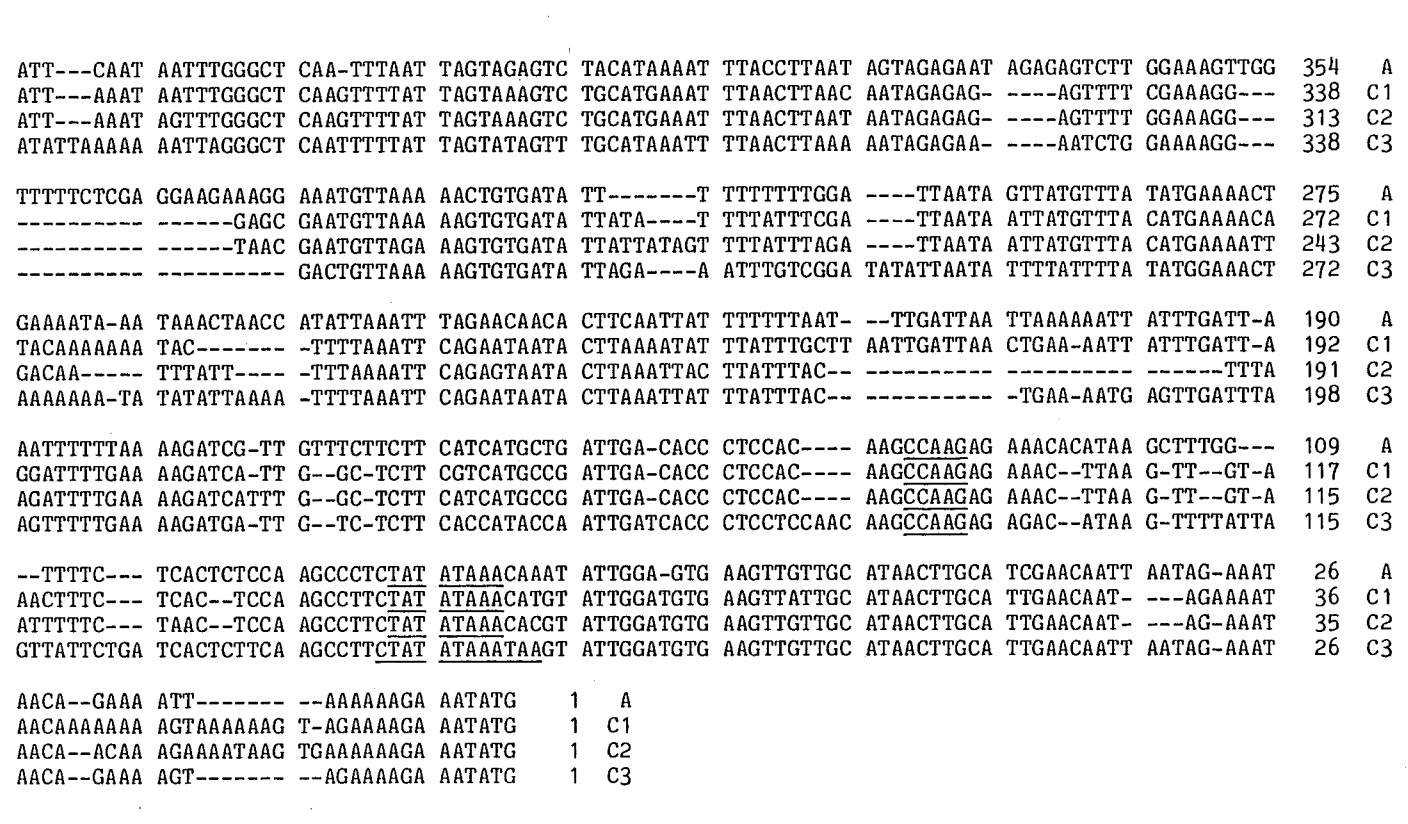
Figure 2:
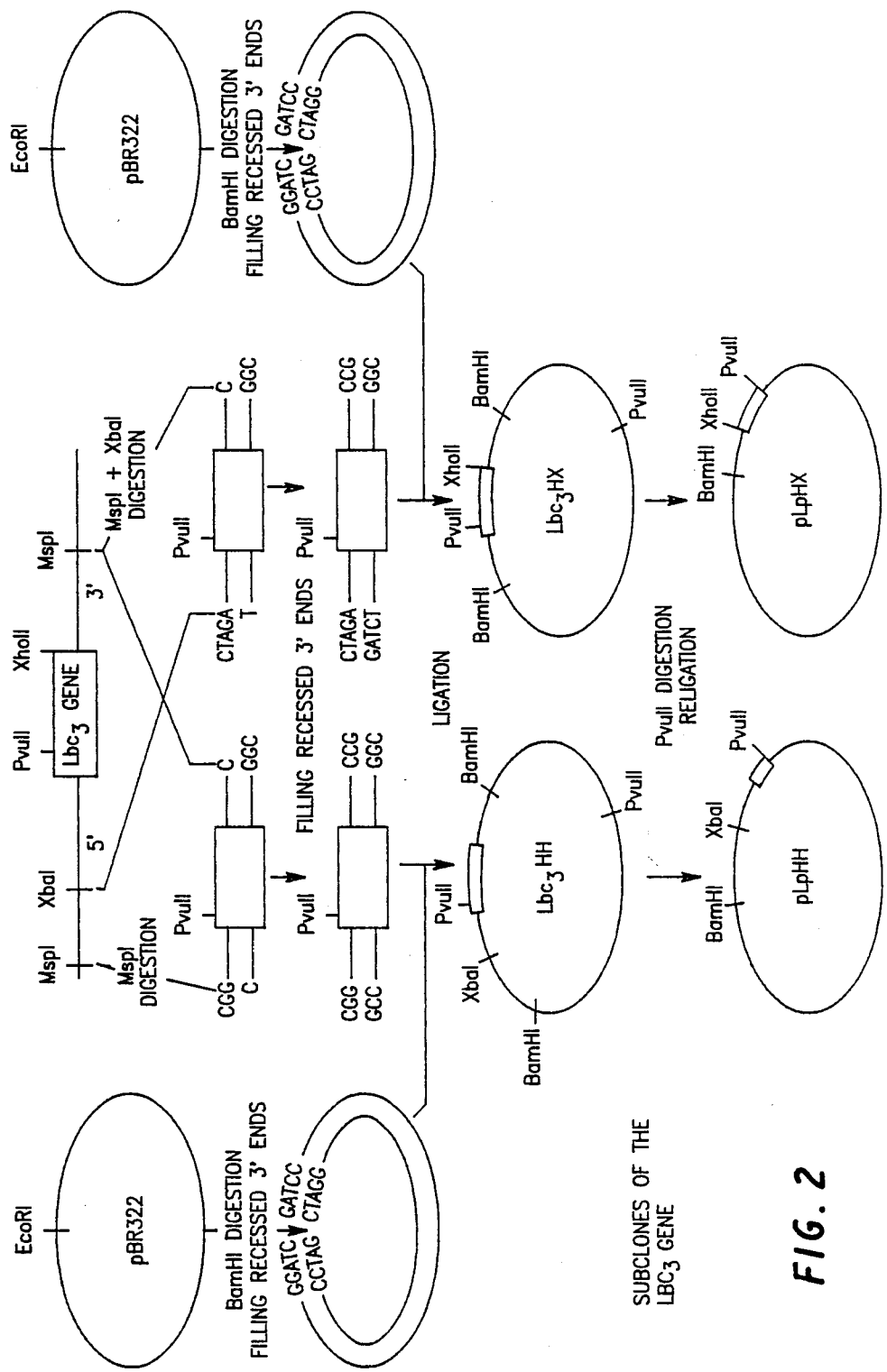
FIG. 2 depicts subcloning the Lbc3 gene.

In accordance with the present invention is presented the sequence of 5' flanking regions of the four soybean leghemoglobin genes Lba, Lbc1, Lbc2, and Lbc3. The sequences are presented in the enclosed sequence scheme, FIG. 1, where the sequences are aligned in such a manner that the homology appears clearly.

In the sequence scheme "-" indicates that no base is present in the position in question. The names of the genes and the base position counted upstream from the ATG start condon are indicated to the right of the sequence scheme. Furthermore the important sequences have been underlined.

As it appears from the sequence scheme a distinct degree of homology exists between the four 5' flanking regions, and in the position 23-24 bp upstream from the CAP addition site they all contain a TATATAAA sequence corresponding to the "TATA" box which is eucaryotic cells usually are located a corresponding number of bp upstream from the CAP addition site. Furthermore a CCAAG sequence is present 64-72 bp upstream from the CAP addition site, said sequence corresponding to the "CCAAT" box usually located 70-90 bp upstream from the CAP addition site. From the CAP addition site to the translation start codon, ATG, leader sequences of 52-59 bp are present and show a distinct degree of homology of approx. 75-80%.

In accordance with the present invention it has furthermore been proved, exemplified by Lbc3, that the 5' flanking regions of the soybean leghemoglobin genes are functionally active in yeast. The latter has been proved by fusing the *E. coli* chloroamphenicol acetyl transferase (CAT) gene with the 5' and 3' flanking regions of the soybean Lbc3 gene in such a manner that the expression of the CAT gene is controlled by the Lb promoter. The fusion fragment was inserted in the yeast plasmid vector, YEP 24, comprising the yeast URA-3 gene as a selectable marker. The yeast strain *S. cerevisiae* TM1 which is URA-3 and unable to synthesize heme due to a mutation in the δ-amino levulinic acid synthetase gene, δ-ALA, was subsequently transformed with the resulting construction. The transformed yeast cells showed a CAT activity under all growth conditions tested. The conclusion can therefore be made that the 5' flanking regions of soybean leg hemglobin genes are functional in yeast.

In accordance with the present invention it has furthermore been proved that the 5' flanking regions act as target for a regulation exerted or mediated by intracellular heme. The CAT activity is thus 20–40 fold higher in the yeast *S. cerevisiae* TM1 grown in the presence of δ-ALA than the CAT activity in yeast grown without this heme precursor in the growth medium. Similar high CAT activities were present in the yeast *S. cerevisiae* TM1 grown in the presence of heme, protoporphyrin IX, or the heme analog deuteroporphyrin IX. The effect of heme on the CAT activity is specific since the amount of the URA-3 gene product remains constant under all the conditions tested. Furthermore the transcriptional level does not apparently change because of the presence of heme as the CAT-mRNA level remains constant independent of changes in the intracellular heme concentration. It can therefore be concluded that the regulatory mechanism exerted or mediated by heme occurs on the posttranscriptional level.

The observed increase of CAT activity is dependent on protein synthesis. The half life of the CAT enzyme is furthermore independent of the presence of heme, and in vitro CAT activity is not stimulated by heme. Therefore heme most likely regulates the gene expression on the translational level. A fusion of the 5' flanking region of Lbc3 with coding region of the neomycine phospho transferase (neo) gene, is controlled by heme is a completely similar manner as the CAT gene fused with a 5' flanking region of the Lbc3 gene. The effect of heme is thus not mediated by heme interacting with the coding sequence, but rather by heme interacting with the 5' or 3' flanking Lbc3 sequences present in the CATmRNA. The expression of a gene only containing the Lbc3 5' flanking region and the neo gene is controlled in a similar manner by heme. The effect of intracellular heme on the gene expression can thus be mediated by an interaction with the leader sequence.

The short leader sequences do not contain translation start codons. The regulatory mechanism exerted or mediated by intracellular heme is therefore not related to regulatory mechanisms involving false start codons, cf. the disclosure of Hunt, T. Nature, Vol. 316, 580–581, (1985). The regulatory mechanism described in relation to the present invention is exerted or mediated by heme interacting with a leader sequence and is therefore a novel regulatory mechanism.

The presence of plasmids in a cell present in a natural environment provides the cell with a property which is only advantageous for the cell under certain circumstances. Plasmid encoded properties may for instance be resistance to an antibiotic present in the surrounding environment. The presence of a plasmid and synthesis of the plasmid encoded gene products do, however, also load the energy metabolism of the cell and the protein synthesis apparatus, and a cell containing a plasmid is therefore ousted and lost in an environment not needing the plasmid encoded properties.

The above mentioned instability is additionally increased by using plasmids as vectors for synthesis of a desired gene product not usually produced by the cell in question. The latter implies tha cells synthesizing such products must be subjected to a selection pressure in order to ensure that the desired gene product can still by synthesized. The previous method of achieving a high expresion of a certain gene product is that the expression is controlled by a strong promoter causing a high concentration of the mRNA being translated into the gene product in question.

A high concentration of gene product can, however, also be obtained by a more efficient translation of the mRNA in question. The latter implies that the gene product synthesis is controlled both at the transcriptional and on the translation level, which means that the genetic load on a cell synthesizing a certain gene product can be distributed on two activities instead of one as usually.

The two activities can therefore be manipulated in such a manner that the same result concerning concentration of gene product can be obtained though the promoter is not as strong as the promoters usually employed. Such a distribution of the two activities implies that the cell is not as genetically loaded as when the gene product synthesis is only controlled by one strong promoter. As a result the selection pressure on the cell in question can be reduced.

It is furthermore of importance to obtain the utilization most rational for the cell of the energy metabolism and of the protein synthesis apparatus in the phase where the synthesis of the desired gene product occurs. Such a rational utilization of the energy metabolism and of the protein synthesis apparatus is improved preferably by optimizing the late steps of the synthesis of a gene product rather than optimating the early steps.

An important feature of a gene expression system is therefore that the expression of the desired product can be increased from an initially low expression to an overproduction by a manipulation of the external environment of the cell as disclosed by the present invention. Furthermore an inducible optimizing of the posttranscriptional synthesis steps—which has been disclosed by the present invention—is more advantageous than an induced optimization of the transcription.

Previous methods for the expression of genes in yeast employ a range of promoters and expression vectors, cf. for instance EP 120 551 A2, in which the use of GAPDH- or PyK-yeast promoters is disclosed, as well as of expression vectors comprising these promoters.

GB No. 2,137,208 A discloses furthermore the use of the promoter GAL1 in several expression vectors.

When using these previously known promoters, the expression can only be increased by increasing the transcription-initiation frequency. The use of these promoters involves consequently a high genetic load on the cell, an irrational utilization of the energy metabolism and the synthesis apparatus, as well as a resulting instability necessitating a high selection pressure on the host organism when using these promoters.

The object of the present invention is therefore to disclose a method of using novel promoters active in yeast, as well as leader sequences subjecting in a novel manner the expression of the following gene to a regulation at the posttranscriptional level. Further objects of the invention are to provide combinations of the promoter and leader sequence, whereby these combinations have been obtained from 5' flanking regions of plant leghemoglobin genes and proved to be functional in yeast, as well as it is an object of the invention to provide plasmids comprising the above combination of promoter and leader sequences.

The method according to the present invention is characterized by using a first DNA fragment comprising a leader sequence, in combination with a second DNA fragment comprising a promoter sequence, said combination increasing at high intracellular concentrations of heme the expression of a desired gene by increasing the translation efficiency. In this manner it is possible by inserting a gene downstream from the combination and in a suitable vector being able to replicate in yeast to obtain a synthesis of a biologically active product. This method allows an increase of the expression of a desired gene by a novel regulatory mechanism acting at the posttranscriptional level. As a particular result a reduced genetic strain of the host cell and an optimal utilization of the protein synthesis apparatus and the energy metabolism of the host cell is obtained and consequently an increased stability of the expression vector in the host cell.

A particular embodiment of the method according to the invention uses as a first DNA fragment an isolated or synthesized leader sequence to be combined with a second isolated or synthesized DNA fragment. In this manner it is possible to combine any leader sequence from yeast, plants or animals under natural conditions being subjected to a posttranscriptional regulation with any suited yeast promoter, plant promoter or another promoter being functional in yeast.

According to a particular embodiment of the method according to the invention the intracellular concentration of heme is increased by adding to the growth medium such carbon sources, especially non-fermentable carbon sources, which cause increased intracellular concentrations of heme. In this manner an induction of the expression of the desired gene is obtained by adding a carbon source to the growth medium. Examples of such carbon sources are glycerol and succinate which are particularly preferred because they are inexpensive and easily available carbon sources. Furthermore ethanol can be used. Under certain circumstances the yeast itself can produce this ethanol while growing. After termination of the growth the ethanol is utilized whereby the translation is increased.

According to a special embodiment the same effect can be obtained by the intracellular concentration of heme being increased by adding to the growth medium one or several substances selected from the group consisting of heme, heme analogs, and heme precursors. An example of a heme analog is deuteroporphyrin IX, and an example of a heme precursor is α-amino levulinic acid.

In this manner a simple access to a combination of leader sequence and promoter sequence is obtained, said combination being proved according to the present invention to be functional in yeast. Examples of such DNA fragments are the four 5' flanking regions of the soybean leghemoglobin genes, viz.

| Lba with the sequence: | | | | |
|---|---|---|---|---|
| GAGATACATT | ATAATAATCT | CTCTAGTGTC | TATTTATTAT | TTTATCTGGT |
| GATATATACC | TTCTCGTATA | CTGTTATTTT | TTCAATCTTG | TAGATTTACT |
| TCTTTTATTT | TTATAAAAAA | GACTTTATTT | TTTTAAAAAA | AATAAAGTGA |
| ATTTTGAAAA | CATGCTCTTT | GACAATTTTC | TGTTTCCTTT | TTCATCATTG |
| GGTTAAATCT | CATAGTGCCT | CTATTCAATA | ATTTGGGCTC | AATTTAATTA |
| GTAGAGTCTA | CATAAAATTT | ACCTTAATAG | TAGAGAATAG | AGAGTCTTGG |
| AAAGTTGGTT | TTTCTCGAGG | AAGAAAGGAA | ATGTTAAAAA | CTGTGATATT |
| TTTTTTTTGG | ATTAATAGTT | ATGTTTATAT | GAAAACTGAA | AATAAATAAA |
| CTAACCATAT | TAAATTTAGA | ACAACACTTC | AATTATTTTT | TTAATTTGAT |
| TAATTAAAAA | ATTATTTGAT | TAAATTTTTT | AAAAGATCGT | TGTTTCTTCT |
| TCATCATGCT | GATTGACACC | CTCCACAAGC | CAAGAGAAAC | ACATAAGCTT |
| TGGTTTTCTC | ACTCTCCAAG | CCCTCTATAT | AAACAAATAT | TGGAGTGAAG |
| TTGTTGCATA | ACTTGCATCG | AACAATTAAT | AGAAATAACA | GAAAATTAAA |
| AAAGAAATAT | G, | | | |
| Lbc1 with the sequence: | | | | |
| TTCTCTTAAT | ACAATGGAGT | TTTTGTTGAA | CATACATACA | TTTAAAAAAA |
| AATCTCTAGT | GTCTATTTAC | CCGGTGAGAA | GCCTTCTCGT | GTTTTACACA |
| CTTTAATATT | ATTATATCCT | CAACCCCACA | AAAAAGAATA | CTGTTATATC |
| TTTCCAAACC | TGTAGATTTA | TTTATTTATT | TATTTATTTT | TACAAAGGAG |
| ACTTCAGAAA | AGTAATTACA | TAAAGATAGT | GAACATCATT | TTATTTATTA |
| TAATAAACTT | TAAAATCAAA | CTTTTTTATA | TTTTTTGTTA | CCCTTTTCAT |
| TATTGGGTGA | AATCTCATAG | TGAAGCCATT | AAATAATTTG | GGCTCAAGTT |
| TTATTAGTAA | AGTCTGCATG | AAATTTAACT | TAACAATAGA | GAGAGTTTTC |
| GAAAGGGAGC | GAATGTTAAA | AAGTGTGATA | TTATATTTTA | TTTCGATTAA |
| TAATTATGTT | TACATGAAAA | CATACAAAAA | AATACTTTTA | AATTCAGAAT |
| AATACTTAAA | ATATTTATTT | GCTTAATTGA | TTAACTGAAA | ATTATTTGAT |
| TAGGATTTTG | AAAAGATCAT | TGGCTCTTCG | TCATGCCGAT | TGACACCCTC |
| CACAAGCCAA | GAGAAACTTA | AGTTGTAAAC | TTTCTCACTC | CAAGCCTTCT |
| ATATAAACAT | GTATTGGATG | TGAAGTTATT | GCATAACTTG | CATTGAACAA |
| TAGAAAATAA | CAAAAAAAAG | TAAAAAAGTA | GAAAAGAAAT | ATG, |
| Lbc2 with the sequence: | | | | |
| TCGAGTTTTT | ACTGAACATA | CATTTATTAA | AAAAAACTCT | CTAGTGTCCA |
| TTTATTCGGC | GAGAAGCCTT | CTCGTGCTTT | ACACACTTTA | ATATTATTAT |
| ATCCCCACCC | CCACCAAAAA | AAAAAAAACT | GTTATATCTT | TCCAGTACAT |
| TTATTTCTTA | TTTTTACAAA | GGAAACTTCA | CGAAAGTAAT | TACAAAAAAG |
| ATAGTGAACA | TCATTTTTTT | AGTTAAGATG | AATTTTAAAA | TCACACTTTT |
| TTATATTTTT | TTGTTACCCT | TTTCATTATT | GGGTGAAATC | TCATAGTGAA |
| ACTATTAAAT | AGTTTGGGCT | CAAGTTTTAT | TAGTAAAGTC | TGCATGAAAT |
| TTAACTTAAT | AATAGAGAGA | GTTTTGGAAA | GGTAACGAAT | GTTAGAAAGT |
| GTGATATTAT | TATAGTTTTA | TTTAGATTAA | TAATTATGTT | TACATGAAAA |
| TTGACAATTT | ATTTTTAAAA | TTCAGAGTAA | TACTTAAATT | ACTTATTTAC |
| TTTAAGATTT | TGAAAAGATC | ATTTGGCTCT | TCATCATGCC | GATTGACACC |
| CTCCACAAGC | CAAGAGAAAC | TTAAGTTGTA | ATTTTTCTAA | CTCCAAGCCT |
| TCTATATAAA | CACGTATTGG | ATGTGAAGTT | GTTGCATAAC | TTGCATTGAA |
| CAATAGAAAT | AACAACAAAG | AAAATAAGTG | AAAAAAGAAA | TATG, |
| and Lbc3 with the sequence: | | | | |
| TATGAAGATT | AAAAAATACA | CTCATATATA | TGCCATAAGA | ACCAACAAAA |
| GTACTATTTA | AGAAAGAAA | AAAAAAACCT | GCTACATAAT | TTCCAATCTT |
| GTAGATTTAT | TTCTTTTATT | TTTATAAAGG | AGAGTTAAAA | AAATTACAAA |
| ATAAAAATAG | TGAACATCGT | CTAAGCATTT | TTATATAAGA | TGAATTTTAA |
| AAATATAATT | TTTTTGTCTA | AATCGTATGT | ATCTTGTCTT | AGAGCCATTT |
| TTGTTTAAAT | TGGATAAGAT | CACACTATAA | AGTTCTTCCT | CCGAGTTTGA |
| TATAAAAAAA | ATTGTTTCCC | TTTTGATTAT | TGGATAAAAT | CTCGTAGTGA |
| CATTATATTA | AAAAAATTAG | GGCTCAATTT | TTATTAGTAT | AGTTTGCATA |
| AATTTTAACT | TAAAAATAGA | GAAAATCTGG | AAAAGGGACT | GTTAAAAAGT |
| GTGATATTAG | AAATTTGTCG | GATATATTAA | TATTTTATTT | TATATGGAAA |
| CTAAAAAAAT | ATATATTAAA | ATTTTAAATT | CAGAATAATA | CTTAAATTAT |
| TTATTTACTG | AAAATGAGTT | GATTTAAGTT | TTTGAAAAGA | TGATTGTCTC |
| TTCACCATAC | CAATTGATCA | CCCTCCTCCA | ACAAGCCAAG | AGAGACATAA |
| GTTTTATTAG | TTATTCTGAT | CACTCTTCAA | GCCTTCTATA | TAAATAAGTA |
| TTGGATGTGA | AGTTGTTGCA | TAACTTGCAT | TGAACAATTA | ATAGAAATAA |
| CAGAAAAGTA | GAAAAGAAAT | ATG. | | |

A special embodiment of the method according to the invention uses a DNA fragment comprising a promoter sequence and a leader sequence, said DNA fragment being identical with, derived from or comprising 5' flanking regions of plant leghemoglobin genes, yeast genes or other genes subjected to an expression regulation under natural circumstances, said expression regulation being exerted or mediated by intracellular heme.

The present invention deals furthermore with a novel DNA fragment to be used as a first DNA fragment when carrying out the method according to the invention, said fragment being charactreized in that it is a short DNA fragment transcribed into a messenger RNA strand which is a target for a regulation exerted or mediated by intracellular heme. Examples of such DNA fragments are DNA fragments identical with, derived from or comprising a leader sequence from plant leghemoglobin genes, yeast genes or other genes in which said leader sequence under natural circumstances is a target for a regulation exerted or mediated by intracellular heme. Examples thereof are according to the invention DNA fragments which are identical with, derived from or which comprise a leader sequence from the soybean leghemoglobin genes, viz.

The present invention deals furthermore with novel promoter sequences applicable as the second DNA fragment when carrying out the method according to the invention.

This second DNA fragment is characterised in that it is identical with, derived from or comprises a promoter sequence from plant leghemoglobin genes. Examples of such a second DNA fragment are according to the invention DNA fragments identical with, derived from

| Lba with the sequence: | | | | |
|---|---|---|---|---|
| AACTTGCATC TG | GAACAATTAA | TAGTAATAAC | AGAAAATTAA | AAAAGAAATA |
| Lbc1 with the sequence: | | | | |
| AACTTGCATT AGAAATATG, | GAACAATAGA | AAATAACAAA | AAAAAGTAAA | AAAGTAGAAA |
| Lbc2 with the sequence: | | | | |
| AACTTGCATT AAATATG, | GAACAATAGA | AATAACAACA | AAGAAAATAA | GTGAAAAAAG |
| and Lbc3 with the sequence: | | | | |
| AACTTGCATT TG. | GAACAATTAA | TAGAAATAAC | AGAAAGTAG | AAAAGAAATA | or comprising a promoter sequence from soybean leghemoglobin genes, viz.

| Lba with the sequence | | | | |
|---|---|---|---|---|
| GAGATACATT | ATAATAATCT | CTCTAGTGTC | TATTTATTAT | TTTATCTGGT |
| GATATATACC | TTCTCGTATA | CTGTTATTTT | TTCAATCTTG | TAGATTTACT |
| TCTTTTATTT | TTATAAAAAA | GACTTTATTT | TTTTAAAAAA | AATAAAGTGA |
| ATTTTGAAAA | CATGCTCTTT | GACAATTTTC | TGTTTCCTTT | TTCATCATTG |
| GGTTAAATCT | CATAGTGCCT | CTATTCAATA | ATTTGGGCTC | AATTTAATTA |
| GTAGAGTCTA | CATAAAATTT | ACCTTAATAG | TAGAGAATAG | AGAGTCTTGG |
| AAAGTTGGTT | TTTCTCGAGG | AAGAAAGGAA | ATGTTAAAAA | CTGTGATATT |
| TTTTTTTTGG | ATTAATAGTT | ATGTTTATAT | GAAAACTGAA | AATAAATAAA |
| CTAACCATAT | TAAATTTAGA | ACAACACTTC | AATTATTTTT | TTAATTTGAT |
| TAATTAAAAA | ATTATTTGAT | TAAATTTTTT | AAAAGATCGT | TGTTTCTTCT |
| TCATCATGCT | GATTGACACC | CTCCACAAGC | CAAGAGAAAC | ACATAAGCTT |
| TGGTTTTCTC | ACTCTCCAAG | CCCTCTATAT | AAACAAATAT | TGGAGTGAAG |
| TTGTTGCAT, | | | | |
| Lbc1 with the sequence: | | | | |
| TTCTCTTAAT | ACAATGGAGT | TTTTGTTGAA | CATACATACA | TTTAAAAAAA |
| AATCTCTAGT | GTCTATTTAC | CCGGTGAGAA | GCCTTCTCGT | GTTTTACACA |
| CTTTAATATT | ATTATATCCT | CAACCCCACA | AAAAAGAATA | CTGTTATATC |
| TTTCCAAACC | TGTAGATTTA | TTTATTTATT | TATTTATTTT | TACAAAGGAG |
| ACTTCAGAAA | AGTAATTACA | TAAAGATAGT | GAACATCATT | TTATTTATTA |
| TAATAAACTT | TAAAATCAAA | CTTTTTTATA | TTTTTTGTTA | CCCTTTTCAT |
| TATTGGGTGA | AATCTCATAG | TGAAGCCATT | AAATAATTTG | GGCTCAAGTT |
| TTATTAGTAA | AGTCTGCATG | AAATTTAACT | TAACAATAGA | GAGAGTTTTC |
| GAAAGGGAGC | GAATGTTAAA | AAGTGTGATA | TTATATTTTA | TTTCGATTAA |
| TAATTATGTT | TACATGAAAA | CATACAAAAA | AATACTTTTA | AATTCAGAAT |
| AATACTTAAA | ATATTTATTT | GCTTAATTGA | TTAACTGAAA | ATTATTTGAT |
| TAGGATTTTG | AAAAGATCAT | TGGCTCTTCG | TCATGCCGAT | TGACACCCTC |
| CACAAGCCAA | GAGAAACTTA | AGTTGTAAAC | TTTCTCACTC | CAAGCCTTCT |
| ATATAAACAT | GTATTGGATG | TGAAGTTATT | GCAT, | |
| Lbc2 with the sequence: | | | | |
| TCGAGTTTTT | ACTGAACATA | CATTTATTAA | AAAAAACTCT | CTAGTGTCCA |
| TTTATTCGGC | GAGAAGCCTT | CTCGTGCTTT | ACACACTTTA | ATATTATTAT |
| ATCCCCACCC | CCACCAAAAA | AAAAAAAACT | GTTATATCTT | TCCAGTACAT |
| TTATTTCTTA | TTTTTACAAA | GGAAACTTCA | CGAAAGTAAT | TACAAAAAAG |
| ATAGTGAACA | TCATTTTTTT | AGTTAAGATG | AATTTTAAAA | TCACACTTTT |
| TTATATTTTT | TTGTTACCCT | TTTCATTATT | GGGTGAAATC | TCATAGTGAA |
| ACTATTAAAT | AGTTTGGGCT | CAAGTTTTAT | TAGTAAAGTC | TGCATGAAAT |
| TTAACTTAAT | AATAGAGAGA | GTTTTGGAAA | GGTAACGAAT | GTTAGAAAGT |
| GTGATATTAT | TATAGTTTTA | TTTAGATTAA | TAATTATGTT | TACATGAAAA |
| TTGACAATTT | ATTTTTAAAA | TTCAGAGTAA | TACTTAAATT | ACTTATTTAC |
| TTTAAGATTT | TGAAAAGATC | ATTTGGCTCT | TCATCATGCC | GATTGACACC |
| CTCCACAAGC | CAAGAGAAAC | TTAAGTTGTA | ATTTTTCTAA | CTCCAAGCCT |
| TCTATATAAA | CACGTATTGG | ATGTGAAGTT | GTTGCAT, | |
| and Lbc3 with the sequence: | | | | |
| TAACTTGCAT | AAAAAATACA | CTCATATATA | TGCCATAAGA | ACCAACAAAA |
| GTACTATTTA | AGAAAAGAAA | AAAAAAACCT | GCTACATAAT | TTCCAATCTT |
| GTAGATTTAT | TTCTTTTATT | TTTATAAAGG | AGAGTTAAAA | AAATTACAAA |
| ATAAAAATAG | TGAACATCGT | CTAAGCATTT | TTATATAAGA | TGAATTTTAA |
| AAATATAATT | TTTTTGTCTA | AATCGTATGT | ATCTTGTCTT | AGAGCCATTT |
| TTGTTTAAAT | TGGATAAGAT | CACACTATAA | AGTTCTTCCT | CCGAGTTTGA |
| TATAAAAAAA | ATTGTTTCCC | TTTTGATTAT | TGGATAAAAT | CTCGTAGTGA |

-continued

| | | | | |
|---|---|---|---|---|
| CATTATATTA | AAAAAATTAG | GGCTCAATTT | TTATTAGTAT | AGTTTGCATA |
| AATTTTAACT | TAAAAATAGA | GAAAATCTGG | AAAAGGGACT | GTTAAAAAGT |
| GTGATATTAG | AAATTTGTCG | GATATATTAA | TATTTTATTT | TATATGGAAA |
| CTAAAAAAAT | ATATATTAAA | ATTTTAAATT | CAGAATAATA | CTTAAATTAT |
| TTATTTACTG | AAAATGAGTT | GATTTAAGTT | TTTGAAAAGA | TGATTGTCTC |
| TTCACCATAC | CAATTGATCA | CCCTCCTCCA | ACAAGCCAAG | AGAGACATAA |
| GTTTTATTAG | TTATTCTGAT | CACTCTTCAA | GCCTTCTATA | TAAATAAGTA |
| TTGGATGTGA | AGTTGTTGCA | T. | | |

The present invention deals furthermore with novel DNA fragments comprising the combination of a first DNA fragment and a second DNA fragment and to be used when carrying out the method according to the invention.

These DNA fragments are characterized by comprising a promoter sequence and a leader sequence and by being identical with, derived from or comprising 5' flanking regions of plant leghemoglobin genes.

Examples of such DNA fragments according to the invention are DNA fragments comprising a promoter sequence and a leader sequence, and which are identical with, derived from or comprise 5' flanking regions of the soybean leghemoglobin genes, viz.

Lba with the sequence:

| | | | | |
|---|---|---|---|---|
| GAGATACATT | ATAATAATCT | CTCTAGTGTC | TATTTATTAT | TTTATCTGGT |
| GATATATACC | TTCTCGTATA | CTGTTATTTT | TTCAATCTTG | TAGATTTACT |
| TCTTTTATTT | TTATAAAAAA | GACTTTATTT | TTTTAAAAAA | AATAAAGTGA |
| ATTTTGAAAA | CATGCTCTTT | GACAATTTTC | TGTTTCCTTT | TTCATCATTG |
| GGTTAAATCT | CATAGTGCCT | CTATTCAATA | ATTTGGGCTC | AATTTAATTA |
| GTAGAGTCTA | CATAAAATTT | ACCTTAATAG | TAGAGAATAG | AGAGTCTTGG |
| AAAGTTGGTT | TTTCTCGAGG | AAGAAAGGAA | ATGTTAAAAA | CTGTGATATT |
| TTTTTTTTGG | ATTAATAGTT | ATGTTTATAT | GAAAACTGAA | AATAAATAAA |
| CTAACCATAT | TAAATTTAGA | ACAACACTTC | AATTATTTTT | TTAATTTGAT |
| TAATTAAAAA | ATTATTTGAT | TAAATTTTTT | AAAAGATCGT | TGTTTCTTCT |
| TCATCATGCT | GATTGACACC | CTCCACAAGC | CAAGAGAAAC | ACATAAGCTT |
| TGGTTTTCTC | ACTCTCCAAG | CCCTCTATAT | AAACAAATAT | TGGAGTGAAG |
| TTGTTGCATA | ACTTGCATCG | AACAATTAAT | AGAAATAACA | GAAAATTAAA |
| AAAGAAATAT | G, | | | |

Lbc1 with the sequence:

| | | | | |
|---|---|---|---|---|
| TTCTCTTAAT | ACAATGGAGT | TTTTGTTGAA | CATACATACA | TTTAAAAAAA |
| AATCTCTAGT | GTCTATTTAC | CCGGTGAGAA | GCCTTCTCGT | GTTTTACACA |
| CTTTAATATT | ATTATATCCT | CAACCCCACA | AAAAAGAATA | CTGTTATATC |
| TTTCCAAACC | TGTAGATTTA | TTTATTTATT | TATTTATTTT | TACAAAGGAG |
| ACTTCAGAAA | AGTAATTACA | TAAAGATAGT | GAACATCATT | TTATTTATTA |
| TAATAAACTT | TAAAATCAAA | CTTTTTTATA | TTTTTTGTTA | CCCTTTTCAT |
| TATTGGGTGA | AATCTCATAG | TGAAGCCATT | AAATAATTTG | GGCTCAAGTT |
| TTATTAGTAA | AGTCTGCATG | AAATTTAACT | TAACAATAGA | GAGAGTTTTC |
| GAAAGGGAGC | GAATGTTAAA | AAGTGTGATA | TTATATTTTA | TTTCGATTAA |
| TAATTATGTT | TACATGAAAA | CATACAAAAA | AATACTTTTA | AATTCAGAAT |
| AATACTTAAA | ATATTTATTT | GCTTAATTGA | TTAACTGAAA | ATTATTTGAT |
| TAGGATTTTG | AAAAGATCAT | TGGCTCTTCG | TCATGCCGAT | TGACACCCTC |
| CACAAGCCAA | GAGAAACTTA | AGTTGTAAAC | TTTCTCACTC | CAAGCCTTC |
| ATATAAACAT | GTATTGGATG | TGAAGTTATT | GCATAACTTG | CATTGAACAA |
| TAGAAAATAA | CAAAAAAAAG | TAAAAAAGTA | GAAAAGAAAT | ATG, |

Lbc2 with the sequence:

| | | | | |
|---|---|---|---|---|
| TCGAGTTTTT | ACTGAACATA | CATTTATTAA | AAAAAACTCT | CTAGTGTCCA |
| TTTATTCGGC | GAGAAGCCTT | CTCGTGCTTT | ACACACTTTA | ATATTATTAT |
| ATCCCCACCC | CCACCAAAAA | AAAAAAAACT | GTTATATCTT | TCCATTACAT |
| TTATTTCTTA | TTTTTACAAA | GGAAACTTCA | CGAAAGTAAT | TACAAAAAAG |
| ATAGTGAACA | TCATTTTTTT | AGTTAAGATG | AATTTTAAAA | TCACACTTTT |
| TTATATTTTT | TTGTTACCCT | TTTCATTATT | GGGTGAAATC | TCATAGTGAA |
| ACTATTAAAT | AGTTTGGGCT | CAAGTTTTAT | TAGTAAAGTC | TGCATGAAAT |
| TTAACTTAAT | AATAGAGAGA | GTTTTGGAAA | GGTAACGAAT | GTTAGAAAGT |
| GTGATATTAT | TATAGTTTTA | TTTAGATTAA | TAATTATGTT | TACATGAAAA |
| TTGACAATTT | ATTTTTAAAA | TTCAGAGTAA | TACTTAAATT | ACTTATTTAC |
| TTTAAGATTT | TGAAAAGATC | ATTTGGCTCT | TCATCATGCC | GATTGACACC |
| CTCCACAAGC | CAAGAGAAAC | TTAAGTTGTA | ATTTTTCTAA | CTCCAAGCCT |
| TCTATATAAA | CACGTATTGG | ATGTGAAGTT | GTTGCATAAC | TTGCATTGAA |
| CAATAGAAAT | AACAACAAAG | AAAATAAGTG | AAAAAAGAAA | TATG, | and Lbc3 with the sequence:

| | | | | |
|---|---|---|---|---|
| TATGAAGATT | AAAAAATACA | CTCATATATA | TGCCATAAGA | ACCAACAAAA |
| GTACTATTTA | AGAAAGAAA | AAAAAAACCT | GCTACATAAT | TTCCAATCTT |
| GTAGATTTAT | TTCTTTTATT | TTTATAAAGG | AGAGTTAAAA | AAATTACAAA |
| ATAAAAATAG | TGAACATCGT | CTAAGCATTT | TTATATAAGA | TGAATTTTAA |
| AAATATAATT | TTTTTGTCTA | AATCGTATGT | ATCTTGTCTT | AGAGCCATTT |
| TTGTTTAAAT | TGGATAAGAT | CACACTATAA | AGTTCTTCCT | CCGAGTTTGA |
| TATAAAAAAA | ATTGTTTCCC | TTTTGATTAT | TGGATAAAAT | CTCGTAGTGA |
| CATTATATTA | AAAAAATTAG | GGCTCAATTT | TTATTAGTAT | AGTTTGCATA |
| AATTTTAACT | TAAAAATAGA | GAAAATCTGG | AAAAGGGACT | GTTAAAAAGT |
| GTGATATTAG | AAATTTGTCG | GATATATTAA | TATTTTATTT | TATATGGAAA |
| CTAAAAAAAT | ATATATTAAA | ATTTTAAATT | CAGAATAATA | CTTAAATTAT |
| TTATTTACTG | AAAATGAGTT | GATTTAAGTT | TTTGAAAAGA | TGATTGTCTC |
| TTCACCATAC | CAATTGATCA | CCCTCCTCCA | ACAAGCCAAG | AGAGACATAA |
| GTTTTATTAG | TTATTCTGAT | CACTCTTCAA | GCCTTCTATA | TAAATAAGTA |

```
TTGGATGTGA  AGTTGTTGCA  TAACTTGCAT  TGAACAATTA  ATAGAAATAA
CAGAAAAGTA  GAAAAGAAAT  ATG.
```

In addition the invention relates to any plasmid to be used when carrying out the method according to the invention and characterized by comprising a first DNA fragment as previously defined, and a second DNA fragment, also as previously defined. Suitable plasmids according to the invention are YEP Lb CAT and YEP 5 Lb Km. The plasmids according to the invention allow a high expression of a desired gene product by inserting coding sequences for these gene products.

EXAMPLE 1

Sequence Determination Of 5' Flanking Regions Of Soybean Leghemoglobin Genes

From a soybean gene library the four soybean leghemoglobin genes Lba, Lbc1, Lbc2, and Lbc3 are provided as described by Jensen, E.O. et al., Nature Vol. 291, No. 3817, 677–679 (1981). The 5' flanking regions of the four soybean leghemoglobin genes are isolated, as described by Jensen, E.O., Ph D Thesis, Institut for Molekylaer Biologi, Arhus Universitet (1985), and the sequences of the four 5' flanking regions are determined by the use of the dideoxy chain-termination method as described by Sanger, F., J. Mol. Bio. 143, 161 (1980) and indicated in the sequence scheme.

EXAMPLE 2

Construction of YEP Lb CAT

The construction has been carried out in a sequence of process sections as described below:

Sub-cloning the Lbc3 Gene

The Lbc3 gene was isolated on a 12kb EcoRI restriction fragment from a soybean DNA library, which has been described by Wiborg et al., in Nucl. Acids Res. 10, 3487. A section of the fragment is shown at the top of FIG. 2. This fragment was digested by the enzymes stated so as subsequently to be ligated to pBR322 as indicated in the Figure. The resulting plasmids Lbc3HH and Lbc3HX were subsequently digested by PvuII and religated, which resulted in two plasmids called pLpHH and pLpHX.

Sub-Cloning 5' Flanking Sequences From The Lbc3 Gene

Figure 3:
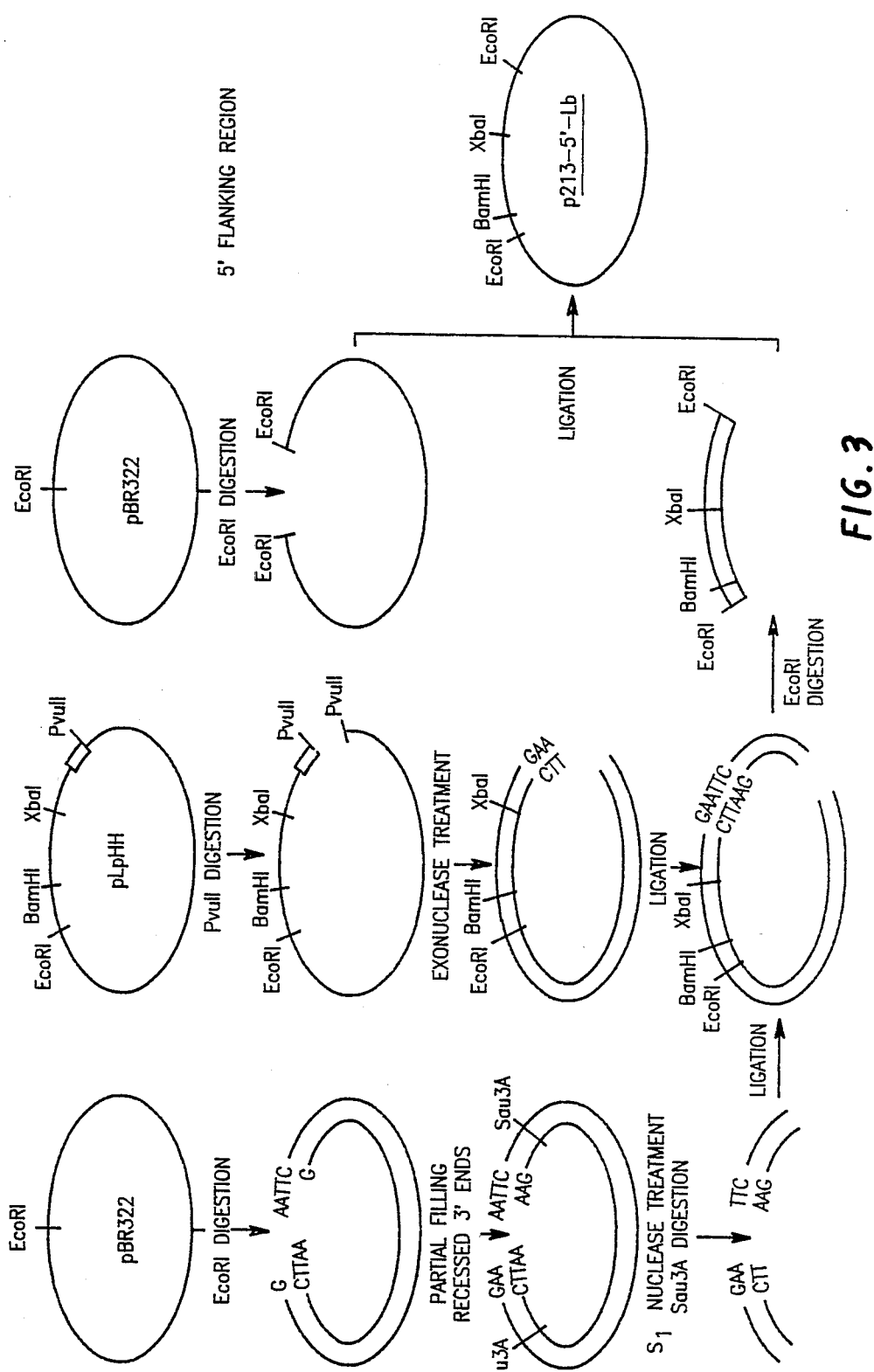
FIG. 3 depicts construction p213-5'-Lb.

For this purpose pLpHH was used as shown in FIG. 3. This plasmid was opened by means of PvuII and treated with exonuclease Ba131. The reaction was stopped at various times and the shortened plasmids were ligated into fragments from pBR322. These fragments had been treated in advance as shown in FIG. 3, in such a manner that in one end they had a DNA sequence

|     |   |
| --- | - |
| TTC | — |
| AAG | — |

After the ligation a digestion with EcoRI took place, and the fragments containing 5' flanking sequences were ligated into EcoRI digested pBR322. These plasmids were transformed into E. coli K803, and the plasmids in the transformants were tested by sequence analysis. A plasmid, p213 5'Lb, isolated from one of the transformants contained a 5' flanking sequence terminating 7 bp before the Lb ATG start condon in such a manner that the sequence is as follows:

| 2kb | |
| --- | --- |
| 5' flanking Lbc3 sequence | AAAGTAGAATTC |

Sub-Cloning 3' Flanking Region Of The Lbc3 Gene

Figure 4:
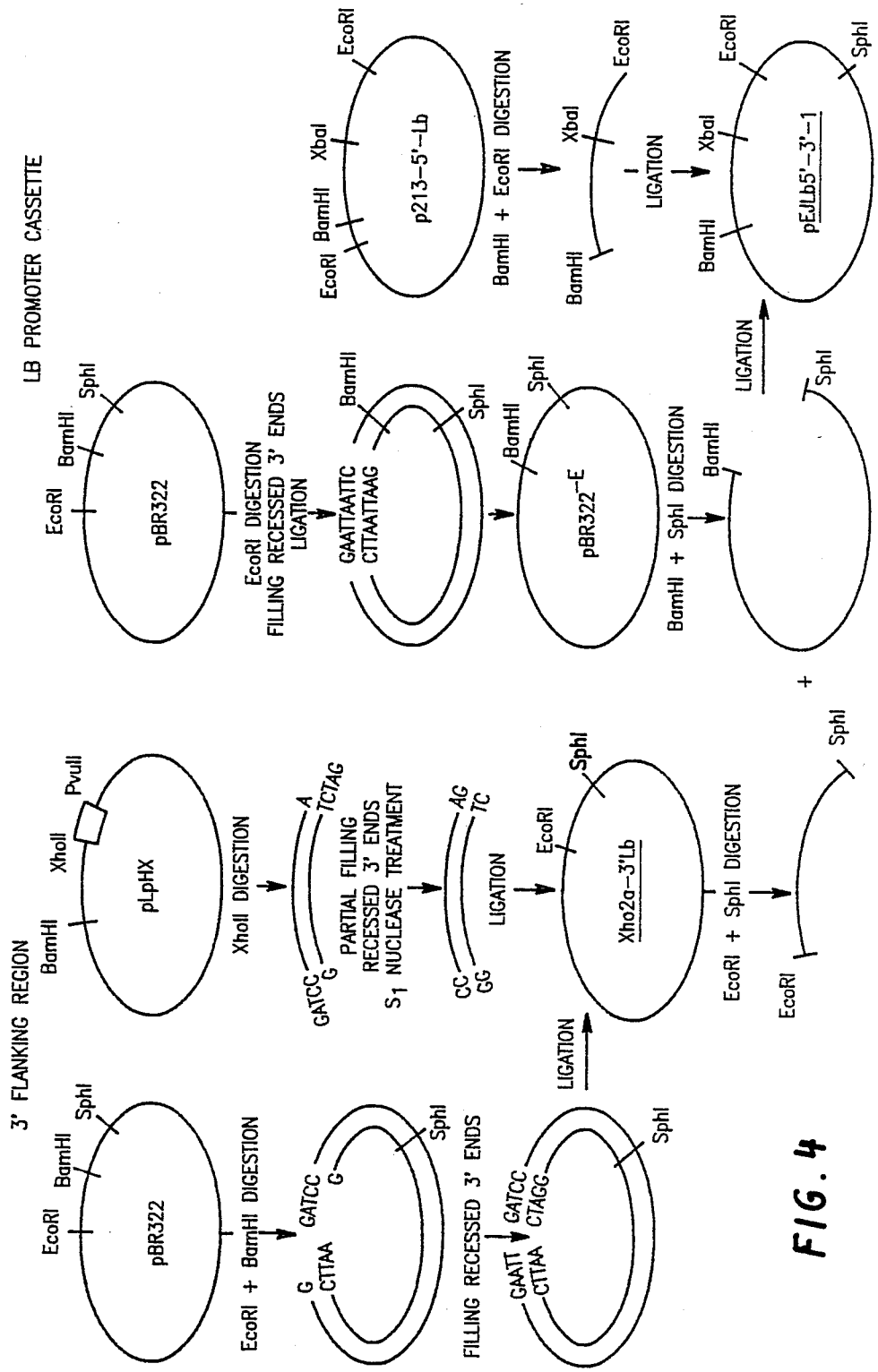
FIG. 4 depicts construction of PEJLb5'-3'-1.

For this purpose pLpHX was used which was digested by XhoII. The ends were partially filled out and excess DNA was removed, as shown in FIG. 4. The fragment shown was ligated into pBR322 which had been pretreated, as shown in the Figure. The construction was transformed into E. coli K803. One of the transformants contained a plasmid called Xho2a-3'Lb. As the XhoII recognition sequence is positioned immediately after the Lb stop codon, cf. FIG. 2, the plasmid contained about 900 bp of the 3' flanking region, and the sequence started with GAATTCTACAA---.

The Construction Of Lb Promoter Cassette

An EcoRI/SphI fragment from Xho2a-3'Lb was mixed with a BamHI/EcoRI fragment from p 213-5'Lb. These two fragments were ligated via the BamHI/SphI cleaving points into a pBR322 derivative where the EcoRI recognition sequence had been removed, cf. FIG. 4. The ligated plasmids were transformed into E. coli K803. A plasmid in one of the transformants contained the correct fragments, and it was called pEJLb 5'-3'-1.

Construction Of Chimeric Lb/CAT Gene

Figure 5:
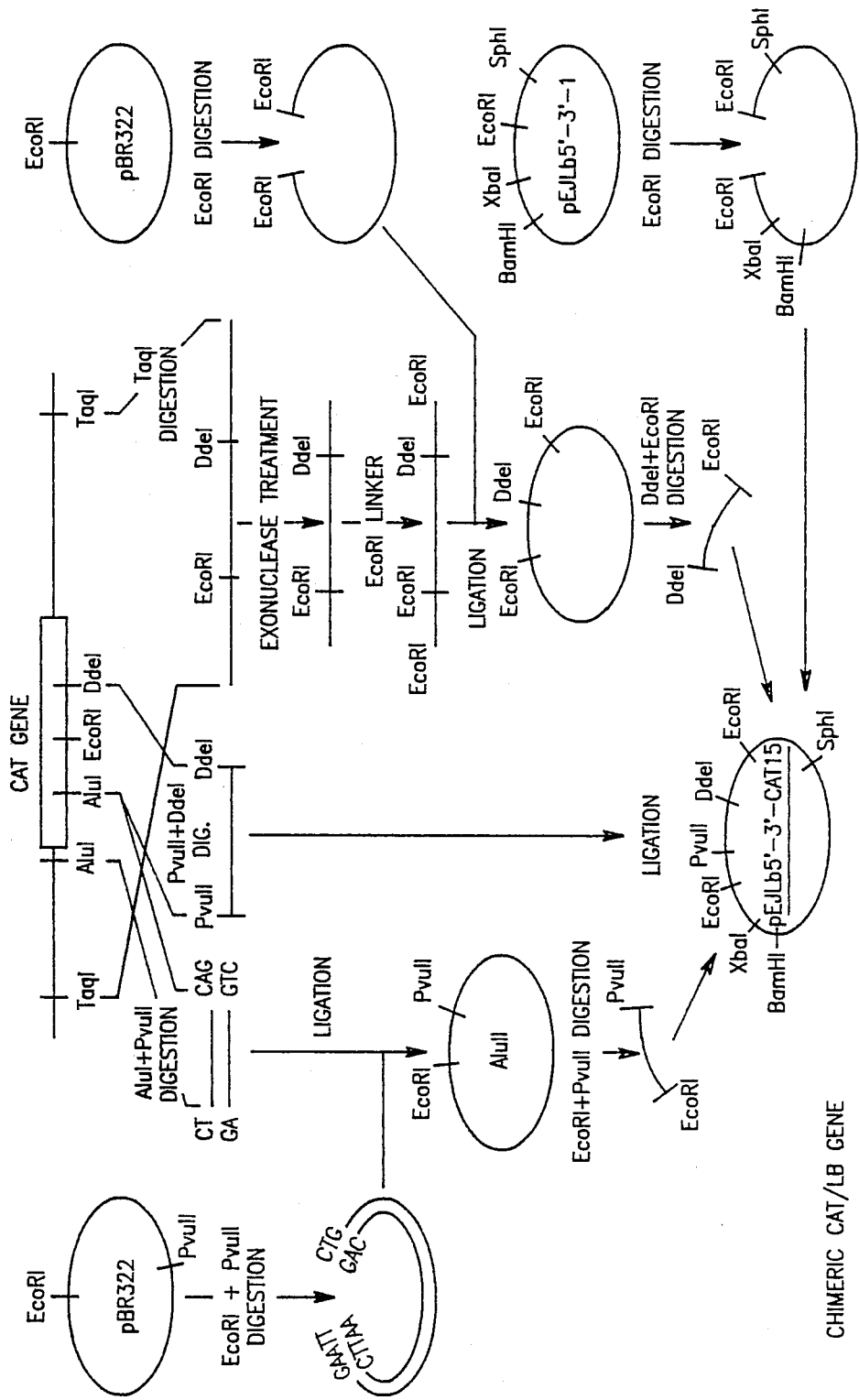
FIG. 5 depicts construction of PEJLb5'-3'-CAT15.

The CAT gene of pBR322 was isolated on several smaller restriction fragments, as shown in FIG. 5. The 5' coding region was isolated on an AluI fragment which was subsequently ligated into pBR322 and treated as stated in the Scheme. This was transformed into E. coli K803, and a selected transformant contained a plasmid called Alu11. The 3' coding region was isolated on a TaqI fragment. This fragment was treated with exonuclease Ba13, whereafter EcoRI linkers were added. Then followed a digestion with EcoRI and a ligation into EcoRI digested pBR322. The latter was transformed into E. coli K803 and the transformants were analyzed. A plasmid, Taq 12, contained the 3' coding region of the CAT gene plus 23 bp 3' flanking sequences so as subsequently to terminated in the following sequence.

—CCCCGAATTC.

Subsequently the following fragments were ligated together into EcoRI digested pEJLb5'-3'-1: EcoRI/PvuII fragment from Alu11, PvuII/DouI fragment from pBR322 and DdeI/EcoRI fragment from Taq 12. The latter was transformed into E. coli K803. A selected transformant contained the correct plasmid called pEJLb 5'-3' CAT 15.

Cloning Chimeric Lb/CAT Gene In Yeast Plasmid

Figure 6:
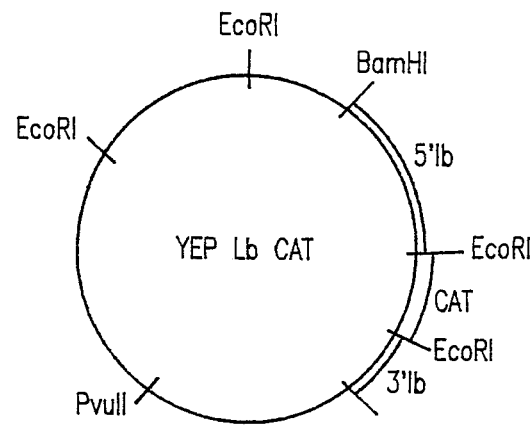
FIG. 6 depicts YEP Lb CAT.

This chimeric gene was isolated on a BamHI/SalI fragment from pEJLb 5'-3' CAT 15 and ligated into the yeast plasmid YEP24 cut with the same enzymes. After the transformation into *E. coli* K803 a selected transformant was examined. It contained the plasmid YEP LbCAT shown in FIG. 6. This plasmid was further transformed into the yeast strains *Saccharomyces cerevisiae* DBY747 and TM1.

EXAMPLE 3

Construction of YEP 5Lb Km

Figure 8:
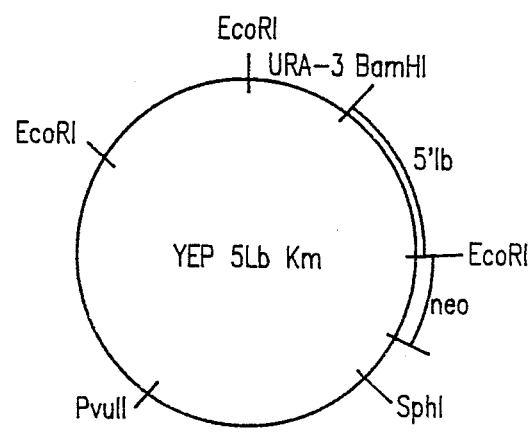
FIG. 8 depicts YEP 5Lb Km.
Figure 7:
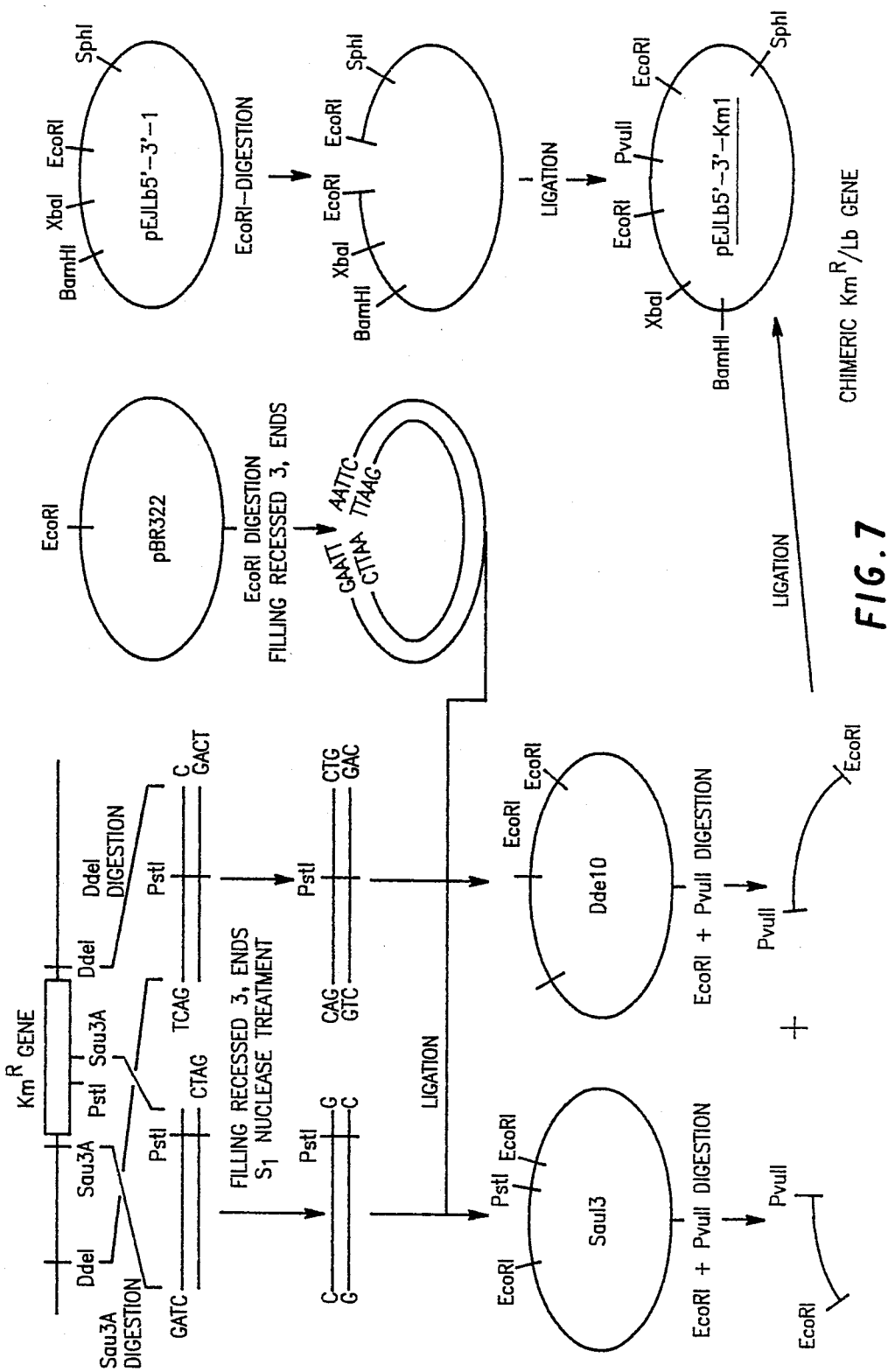
FIG. 7 depicts construction of PEJLb5'-3'-Kml.

The neomycine phosphotransferase (NPTII) gene was isolated from pKM2 (Beck. et al., Gene 19, 327). The 5' coding region was isolated on a Sau3A fragment, as shown in FIG. 7, and subsequently ligated into pBR322 resulting in a plasmid called Sau 13. The 3' coding and flanking region was isolated on a PvuII fragment. The latter was together with a EcoRI/PvuIi fragment from Sau 13 ligated into EcoRI/PvuII digested pEJLB 5'-3'-1. Upon transformation into E. coli K803 a transformant with the correct plasmid, pEJLb 5' Km 1, was selected. This plasmid was later on digested by means of BamHI and partially by means of PvuII in such a manner that the entire 5' flanking Lb sequence +the coding NPTII sequence were present on a BamHI/PvuII fragment. This fragment was ligated into BamHI/PvuII digested YEP24 resulting in the plasmid YEP 5Lb Km shown in FIG. 8. This plasmid was transformed into the yeast strain Saccharomyces cerevisiae Tm1.

EXAMPLE 4

The Effect Of Carbon Source On Expression of CAT

Saccharomyces cerevisiae DBY747 containing the plasmid YEP Lb CAT is grown in minimum medium plus 2% of a carbon source. The cells are harvested at a cellular density of $5 \times 10^6$ cells per ml. The CAT activity is measured as described by Walker, Edlund, Boulet & Rutter, Nature, 306, 557 (1983).

In Table 1 the CAT activity has been indicated as a function of the carbon source. The highest activity obtained by growing on succinate and glycerol has been arbitrarily set to 100%.

TABLE 1

| Carbon Source | Activity |
| --- | --- |
| Succinate | 100 |
| Glycerol | 100 |
| Glucose | 28 |
| Sucrose | 18 |

EXAMPLE 5

The effect of heme precursors and heme analogs on the induction of gene expression.

Saccharomyces cerevisieae TM1 containing the plasmid YEP Lb CAT is grown in a minimum medium plus 2% glucose plus 0.1% Tween ® plus 20 μg/ml ergosterol plus 50 μg/ml methionine as well as a heme analog or a heme precursor. Deuteroporphyrin IX (dp) and protoporphyrin (pp), respectively, is added to a final concentration of 5 μg/ml. Hemin is added to a final concentration of 5 μg/ml. α-amino levulinic acid, δ-ALA, is added to a final concentration of 50 μg/ml.

In table 2 the CAT activity has been indicated as the activity of heme precursor and heme analog, respectively. the highest activity obtained by adding δ-ALA or dp has arbitrarily been set to 100%.

TABLE 2

| Inducer | CAT activity |
| --- | --- |
| Glucose + δ-ALA | 100 |
| Glucose + dp | 100 |
| Glucose + pp | 50 |
| Glucose + hemin | 25 |
| Glucose | 5 |

It is obvious that the patent protection of the present invention is not restricted to the Examples indicated here.

Thus the invention does not exclusively use 5' flanking regions of soybean leghemoglobin genes. It is well known that the leghemoglobin genes of all leguminous plants have the same activity, cf. Appleby (1974) in The Biology of Nitrogen Fixation, Quispel. A. Ed. North-Holland Publishing Company, Amsterdam Oxford, pages 499–554, and furthermore it has proved for the kidney bean PvLb1 gene that a distinct degree of homology exists with the sequences of soybean Lbc3. Thus the invention comprises the use of 5' flanking regions of leghemoglobin genes from all plants.

According to the invention it is also possible to use such fragments from plants, animals or yeast which under natural conditions exert or mediate the novel regulatory activity described according to the present invention. The latter applies especially to such fragments which can be isolated from DNA fragments from gene libraries by hybridization with labelled sequences from 5' flanking regions of soybean leghemoglobin genes.

It is well known that it is possible to change nucleotide sequences in non-essential subregions of 5' flanking regions without the latter causing a changed promoter activity and regulation. It is also well known that by changing the sequences of important subregions of 5' flanking regions it is possible to change binding affinities between nucleotide sequences and the factors or effector substances necessary for the transcriptional initiation and the translation initiation, and consequently that it is possible to improve the promoter activity and/or regulation. The present invention covers, of course, also the use of such changed sequences of 5' flanking regions. In particular the use of leader sequences can be mentioned which have been extended beyond the natural length provided the use of a such fragments makes the expression of a desired gene product the subject of the novel regulation according to the present invention.

We claim:

1. A method for controlling heterologous gene expression at the post-transcriptional level by heme in Saccharomyces cerevisiae, which method comprises;
    (a) transforming a Saccharomyces cerevisiae yeast with a Saccharomyces cerevisiae expression vector which vector comprises, operably linked from the 5' to the 3' end, a promoter sequence, a soybean leghemoglobin leader sequence, and a heterologous structural gene;
    (b) culturing the transformed yeast in a growth medium under conditions which control the levels of intracellular heme in the transformed yeast thereby resulting in heterologous gene expression being controlled by heme at the post-transcriptional level.

2. The method as claimed in claim 1 wherein said intracellular concentration of heme is increased by adding to the growth medium one or more carbon sources which cause an increased intracellular concentration of heme.

3. The method as claimed in claim 2, wherein the carbon source is selected from the group consisting of glycerol, succinate and ethanol.

4. The method as claimed in claim 1, wherein the intracellular concentration of heme is increased by adding to the growth medium one or more substances selected from the group consisting of heme, heme analogs and heme precursors.

5. The method as claimed in claim 4, wherein said heme analog is deuteroporphyrin IX and said heme precursor is α-amino levulinic acid.

6. The method as claimed in claim 1, wherein the promoter and soybean leghemoglobin leader sequence are both obtained from the soybean Lba gene and jointly comprise the sequence:

| | | | | |
|---|---|---|---|---|
| GAGATACATT | ATAATAATCT | CTCTAGTGTC | TATTTATTAT | TTTATCTGGT |
| GATATATACC | TTCTCGTATA | CTGTTATTTT | TTCAATCTTG | TAGATTTACT |
| TCTTTTATTT | TTATAAAAAA | GACTTTATTT | TTTTAAAAAA | AATAAAGTGA |
| ATTTTGAAAA | CATGCTCTTT | GACAATTTTC | TGTTTCCTTT | TTCATCATTG |
| GGTTAAATCT | CATAGTGCCT | CTATTCAATA | ATTTGGGCTC | AATTTAATTA |
| GTAGAGTCTA | CATAAAATTT | ACCTTAATAG | TAGAGAATAG | AGAGTCTTGG |
| AAAGTTGGTT | TTTCTCGAGG | AAGAAAGGAA | ATGTTAAAAA | CTGTGATATT |
| TTTTTTTTGG | ATTAATAGTT | ATGTTTATAT | GAAAACTGAA | AATAAATAAA |
| CTAACCATAT | TAAATTTAGA | ACAACACTTC | AATTATTTTT | TTAATTTGAT |
| TAATTAAAAA | ATTATTTGAT | TAAATTTTTT | AAAAGATCGT | TGTTTCTTCT |
| TCATCATGCT | GATTGACACC | CTCCACAAGC | CAAGAGAAAC | ACATAAGCTT |
| TGGTTTTCTC | ACTCTCCAAG | CCCTCTATAT | AAACAAATAT | TGGAGTGAAG |
| TTGTTGCATA | ACTTGCATCG | AACAATTAAT | AGAAATAACA | GAAAATTAAA |
| AAAGAAATAT | G. | | | |

7. The method as claimed in claim 1, wherein the promoter and soybean leghemoglobin leader sequence are both obtained from the soybean Lbc1 gene and jointly comprise the sequence:

| | | | | |
|---|---|---|---|---|
| TTCTCTTAAT | ACAATGGAGT | TTTTGTTGAA | CATACATACA | TTTAAAAAAA |
| AATCTCTAGT | GTCTATTTAC | CCGGTGAGAA | GCCTTCTCGT | GTTTTACACA |
| CTTTAATATT | ATTATATCCT | CAACCCCACA | AAAAAGAATA | CTGTTATATC |
| TTTCCAAACC | TGTAGATTTA | TTTATTTATT | TATTTATTTT | TACAAAGGAG |
| ACTTCAGAAA | AGTAATTACA | TAAAGATAGT | GAACATCATT | TTATTTATTA |
| TAATAAACTT | TAAAATCAAA | CTTTTTTATA | TTTTTTGTTA | CCCTTTTCAT |
| TATTGGGTGA | AATCTCATAG | TGAAGCCATT | AAATAATTTG | GGCTCAAGTT |
| TTATTAGTAA | AGTCTGCATG | AAATTTAACT | TAACAATAGA | GAGAGTTTTC |
| GAAAGGGAGC | GAATGTTAAA | AAGTGTGATA | TTATATTTTA | TTTCGATTAA |
| TAATTATGTT | TACATGAAAA | CATACAAAAA | AATACTTTTA | AATTCAGAAT |
| AATACTTAAA | ATATTTATTT | GCTTAATTGA | TTAACTGAAA | ATTATTTGAT |
| TAGGATTTTG | AAAAGATCAT | TGGCTCTTCG | TCATGCCGAT | TGACACCCTC |
| CACAAGCCAA | GAGAAACTTA | AGTTGTAAAC | TTTCTCACTC | CAAGCCTTCT |
| ATATAAACAT | GTATTGGATG | TGAAGTTATT | GCATAACTTG | CATTGAACAA |
| TAGAAAATAA | CAAAAAAAAG | TAAAAAAGTA | GAAAAGAAAT | ATG. |

8. The method as claimed in claim 1, wherein the promoter and soybean leghemoglobin leader sequence are both obtained from the soybean Lbc2 gene and jointly comprise the sequence:

| | | | | |
|---|---|---|---|---|
| TCGAGTTTTT | ACTGAACATA | CATTTATTAA | AAAAAACTCT | CTAGTGTCCA |
| TTTATTCGGC | GAGAAGCCTT | CTCGTGCTTT | ACACACTTTA | ATATTATTAT |
| ATCCCCACCC | CCACCAAAAA | AAAAAAAACT | GTTATATCTT | TCCAGTACAT |
| TTATTTCTTA | TTTTTACAAA | GGAAACTTCA | CGAAAGTAAT | TACAAAAAAG |
| ATAGTGAACA | TCATTTTTTT | AGTTAAGATG | AATTTTAAAA | TCACACTTTT |
| TTATATTTTT | TTGTTACCCT | TTTCATTATT | GGGTGAAATC | TCATAGTGAA |
| ACTATTAAAT | AGTTTGGGCT | CAAGTTTTAT | TAGTAAAGTC | TGCATGAAAT |
| TTAACTTAAT | AATAGAGAGA | GTTTTGGAAA | GGTAACGAAT | GTTAGAAAGT |
| GTGATATTAT | TATAGTTTTA | TTTAGATTAA | TAATTATGTT | TACATGAAAA |
| TTGACAATTT | ATTTTTAAAA | TTCAGAGTAA | TACTTAAATT | ACTTATTTAC |
| TTTAAGATTT | TGAAAAGATC | ATTTGGCTCT | TCATCATGCC | GATTGACACC |
| CTCCACAAGC | CAAGAGAAAC | TTAAGTTGTA | ATTTTTCTAA | CTCCAAGCCT |
| TCTATATAAA | CACGTATTGG | ATGTGAAGTT | GTTGCATAAC | TTGCATTGAA |
| CAATAGAAAT | AACAACAAAG | AAAATAAGTG | AAAAAAGAAA | TATG. |

9. The method as claimed in claim 1, wherein the promoter and soybean leghemoglobin leader sequence are both obtained from the soybean Lbc3 gene and jointly comprise the sequence:

| | | | | |
|---|---|---|---|---|
| ATAAAAATAG | TGAACATCGT | CTAAGCATTT | TTATATAAGA | TGAATTTTAA |
| AAATATAATT | TTTTTGTCTA | AATCGTATGT | ATCTTGTCTT | AGAGCCATTT |
| TTGTTTAAAT | TGGATAAGAT | CACACTATAA | AGTTCTTCCT | CCGAGTTTGA |
| TATAAAAAAA | ATTGTTTCCC | TTTTGATTAT | TGGATAAAAT | CTCGTAGTGA |
| CATTATATTA | AAAAAATTAG | GGCTCAATTT | TTATTAGTAT | AGTTTGCATA |
| AATTTTAACT | TAAAAATAGA | GAAAATCTGG | AAAAGGGACT | GTTAAAAAGT |
| GTGATATTAG | AAATTTGTCG | GATATATTAA | TATTTTATTT | TATATGGAAA |
| CTAAAAAAAT | ATATATTAAA | ATTTTAAATT | CAGAATAATA | CTTAAATTAT |
| TTATTTACTG | AAAATGAGTT | GATTTAAGTT | TTTGAAAAGA | TGATTGTCTC |

-continued

| | | | | |
|---|---|---|---|---|
| TTCACCATAC | CAATTGATCA | CCCTCCTCCA | ACAAGCCAAG | AGAGACATAA |
| GTTTTATTAG | TTATTCTGAT | CACTCTTCAA | GCCTTCTATA | TAAATAAGTA |
| TTGGATGTGA | AGTTGTTGCA | TAACTTGCAT | TGAACAATTA | ATAGAAATAA |
| CAGAAAAGTA | GAAAAGAAAT | ATG. | | |

10. A Saccharomyces cerevisiae expression vector, which vector comprises; operably linked from the 5′ to the 3′ end; a promotor sequence a soybean leghemoglobin leader sequence, and a heterologous structural gene; which vector when transformed into a suitable Saccharomyces cerevisiae host is capable of conferring upon the host the ability to express the heterologous polypeptide coded for by the heterologous structural gene, wherein the level of expression is regulated at the post-transcriptional level by heme, heme analogs or heme precursors.

11. The vector of claim 10 wherein the promoter is obtained from a soybean leghemoglobin gene.

12. A Saccharomyces cerevisiae yeast which has been transformed with the vector of claim 10.

13. A Saccharomyces cerevisiae yeast which has been transformed with the vector of claim 11.

* * * * *